United States Patent
Maruyama et al.

(10) Patent No.: US 6,369,061 B1
(45) Date of Patent: Apr. 9, 2002

(54) THERAPEUTIC AGENT FOR SPINAL CANAL STENOSIS

(75) Inventors: Tomoyuki Maruyama; Toru Kawamura; Toshiaki Akira, all of Hirakata; Hideaki Kido, Fukuoka; Norifumi Nakamura, Osaka, all of (JP)

(73) Assignees: Mitsubishi Pharma Corporation, Osaka; Nissan Chemical Industries, Ltd., Chiyoda-Ku, both of (JP)

( * ) Notice: Subject to any disclaimer, the term of this patent is extended or adjusted under 35 U.S.C. 154(b) by 0 days.

(21) Appl. No.: 09/786,050

(22) PCT Filed: Aug. 30, 1999

(86) PCT No.: PCT/JP99/04690

§ 371 Date: Mar. 21, 2001

§ 102(e) Date: Mar. 21, 2001

(87) PCT Pub. No.: WO00/12091

PCT Pub. Date: Mar. 9, 2000

(30) Foreign Application Priority Data

Sep. 1, 1998 (JP) .......................... 10-246886

(51) Int. Cl.$^7$ ............................. A61K 31/501
(52) U.S. Cl. ................................. 514/252.03
(58) Field of Search ..................... 514/252.03

(56) References Cited

U.S. PATENT DOCUMENTS

| | | | |
|---|---|---|---|
| 5,202,323 A | 4/1993 | Tanikawa et al. | 514/236.5 |
| 5,314,883 A | 5/1994 | Tanikawa et al. | 514/236.5 |
| 5,750,523 A | 5/1998 | Tanikawa et al. | 514/247 |
| 5,798,357 A | 8/1998 | Ikegawa et al. | 514/252 |

FOREIGN PATENT DOCUMENTS

| | | |
|---|---|---|
| EP | 0 482 208 | 4/1992 |
| JP | 7-285869 | 10/1995 |
| JP | 8-169845 | 7/1996 |
| JP | 9-227411 | 9/1997 |
| WO | 91/16314 | 10/1991 |

OTHER PUBLICATIONS

Database Biosis 'Online! Biosciences Information Service, Philadelphia, PA, US; AN:PREV199089118998, 1990 Morimoto et al.: "Beneficial effec of a slective TXA–2 ...". XP002174554 *abstract* & J.Jap.Orthop.Assoc., Vol. 64, no. 1, 1990, pp. 82–88.

*Primary Examiner*—John M. Ford
(74) *Attorney, Agent, or Firm*—Wenderoth, Lind & Ponack, L.L.P.

(57) ABSTRACT

A therapeutic agent for spinal canal stenosis is provided, which contains a pyridazinone compound of the formula (I)

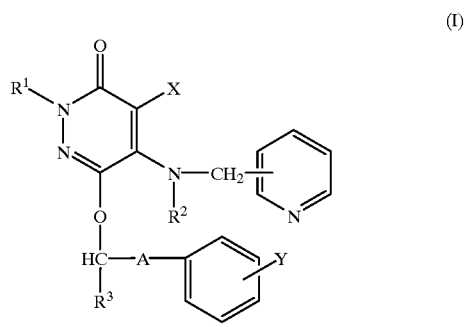

wherein $R^1$, $R^2$ and $R^3$ are each independently a hydrogen atom or a lower alkyl, X is a halogen atom, a cyano or a hydrogen atom, Y is a halogen atom, a trifluoromethyl or a hydrogen atom, and A is a $C_1$–$C_8$ alkylene optionally substituted with a hydroxyl, or its pharmacologically acceptable salt.

3 Claims, 3 Drawing Sheets

THERAPEUTIC AGENT FOR SPINAL CANAL STENOSIS

This application is a 371 PCT/JP99/04690 filed Aug. 30, 1999.

TECHNICAL FIELD

The present invention relates to a therapeutic agent for spinal canal stenosis, which contains a specific pyridazinone compound or its pharmacologically acceptable salt.

BACKGROUND ART

The pyridazinone compound and its salt in the present invention are known to have a superior platelet aggregation inhibitory action, a cardiotonic action, a vasodilating action, an anti-SRS-A (Slow Reacting Substances of Anaphylaxis) action, a thromboxane $A_2$ synthase inhibitory action and the like (JP-B-7-107055, JP-A-7-285869), and are expected as an anti-platelet agent and the like.

However, there are no reports on what effect the pyridazinone compound has on spinal canal stenosis.

The spinal canal stenosis is caused by a pressure on the cauda equina nerve from the stenosed spinal canal due to underdevelopment of spinal canal, spondylosis deformans, degenerative intervertebral discs, degenerative spondylolisthesis, ossification of the yellow ligaments and the like, and is characterized by intermittent claudication. The symptoms of the disease generally surface after middle age when retroplasia begins.

Particularly, lumbar spinal canal stenosis, in which the cauda equina nerve and nerve root in the lumbar portion are compressed, causes lumbago, melosalgia and intermittent claudication.

The cervical spinal canal stenosis generally appears as cervical spondylosis, and shows the symptoms of numbness of fingers, paralysis, spastic walking, paraplegia and the like.

While there are various therapeutics for spinal canal stenosis, including the drug therapy as one of the established therapeutics, a much superior drug therapy is awaited.

DISCLOSURE OF THE INVENTION

It is therefore an object of the present invention to provide a superior therapeutic agent for spinal canal stenosis.

The present inventors have made various studies and found that the pyridazinone compound of the following formula (I) and its pharmacologically acceptable salt have a superior effect on spinal canal stenosis, which resulted in the completion of the present invention.

Accordingly, the present invention provides a therapeutic agent for spinal canal stenosis, which contains a pyridazinone compound of the formula (I)

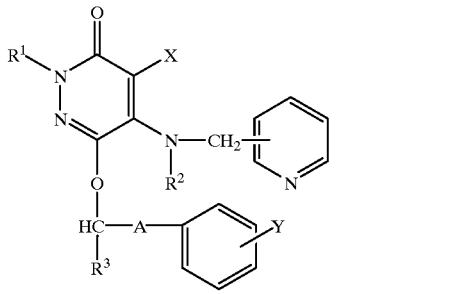

(I)

wherein $R^1$, $R^2$ and $R^3$ are each independently a hydrogen atom or a lower alkyl, X is a halogen atom, a cyano or a hydrogen atom, Y is a halogen atom, a trifluoromethyl or a hydrogen atom, and A is a $C_1$–$C_8$ alkylene optionally substituted with a hydroxyl, or its pharmacologically acceptable salt.

Preferably, the present invention provides a therapeutic agent for spinal canal stenosis, which contains a pyridazinone compound of the formula (I) wherein $R^1$ and $R^2$ are each hydrogen atom, $R^3$ is hydrogen atom or $C_1$–$C_4$ alkyl, X is halogen atom, Y is halogen atom or hydrogen atom, and A is $C_1$–$C_5$ alkylene optionally substituted with hydroxyl, or its pharmacologically acceptable salt.

A particularly preferable example of the pyridazinone compound of the formula (I) is 4-bromo-6-[3-(4-chlorophenyl)propoxy]-5-(3-pyridylmethylamino)-3(2H)-pyridazinone.

DETAILED DESCRIPTION OF THE INVENTION

Figure 1:
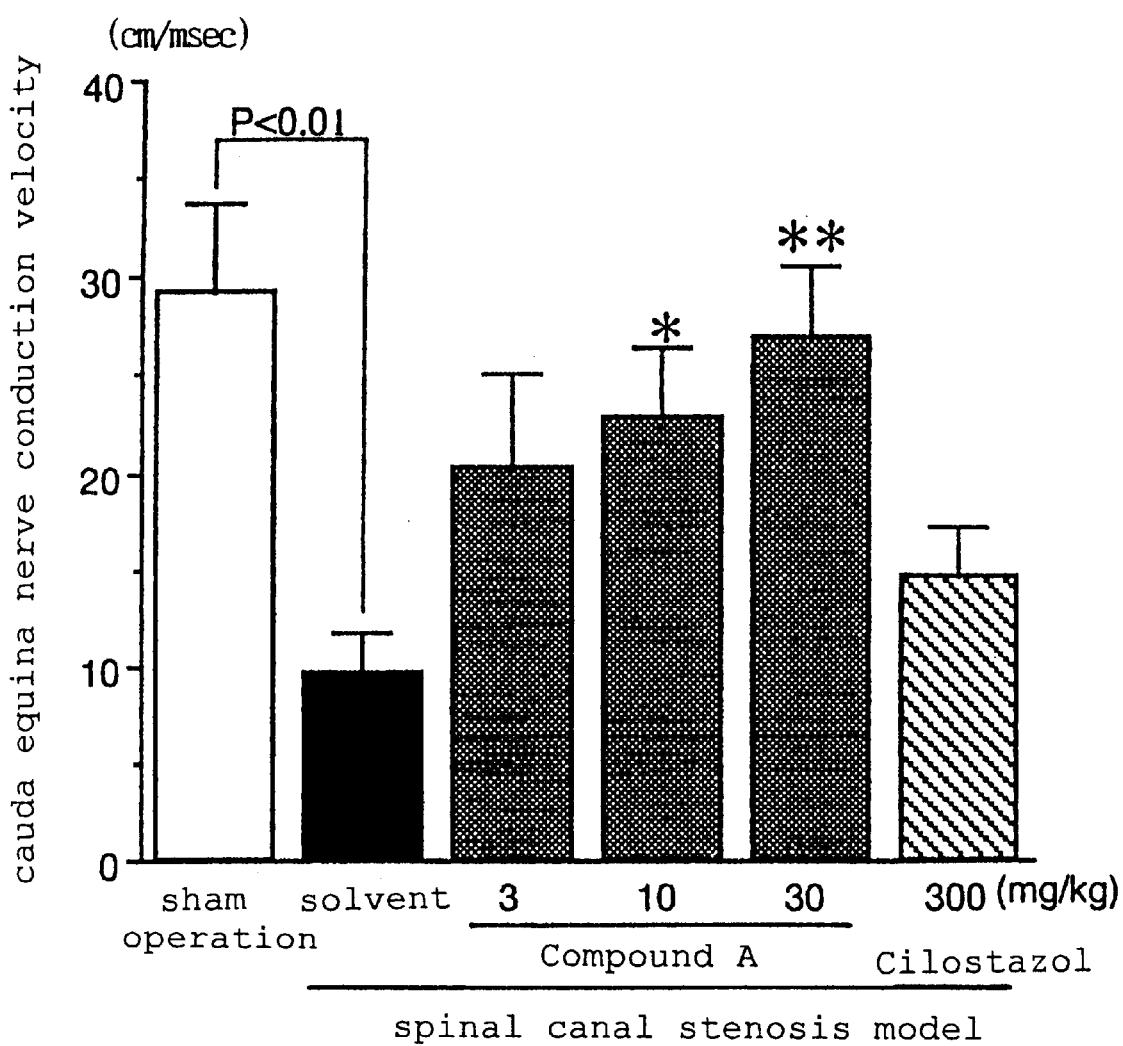
FIG. 1 shows a comparison of the effects of 4-bromo-6-[3-(4-chlorophenyl)propoxy]-5-(3-pyridylmethylamino)-3(2H)-pyridazinone hydrochloride (hereinafter to be also referred to as compound A) and cilostazol on cauda equina nerve conduction velocity in a rabbit acute spinal canal stenosis model, wherein * means that a significant difference of $p<0.05$ was obtained as a result of the Dunnett's method to a solvent group as a control, and ** means that a significant difference of $p<0.01$ was obtained as a result of the Dunnett's method to a solvent group as a control. Note that $P<0.01$ means that a significant difference of $p<0.01$ was obtained as a result of the Student's t-test to a sham operation group.

The respective symbols used in this specification are explained in the following.

The lower alkyl at $R^1$, $R^2$ and $R^3$ is linear or branched chain alkyl having 1 to 6 carbon atoms, which is exemplified by methyl, ethyl, n-propyl, isopropyl, n-butyl, isobutyl, sec-butyl, t-butyl, pentyl, hexyl and the like.

$R^1$ and $R^2$ are each preferably hydrogen atom, and Re is preferably hydrogen atom or alkyl having 1 to 4 carbon atoms.

The alkyl having 1 to 4 carbon atoms at $R^3$ is exemplified by methyl, ethyl, n-propyl, isopropyl, n-butyl, isobutyl, sec-butyl, t-butyl and the like.

The halogen atom at X and Y is fluorine atom, chlorine atom, bromine atom or iodine atom.

Preferable X is halogen atom, and preferable Y is halogen atom or hydrogen atom.

The alkylene having 1 to 8 carbon atoms at A, which is optionally substituted with hydroxyl group, may be linear or branched chain alkylene. Examples thereof include methylene, ethylene, propylene, butylene, pentylene, hexylene, heptylene, octylene, 2,2-dimethylethylene, 2,2-diethylethylene, 2,2-di-n-propylethylene, hydroxymethylene, 1-hydroxyethylene, 2-hydroxyethylene, 3-hydroxypropylene and the like.

Preferable A is alkylene having 1 to 5 carbon atoms, which is optionally substituted with hydroxyl.

In the formula (I), the bonding site of methylene and pyridine ring is not particularly limited, but it is preferably the 3-position relative to the nitrogen atom of the pyridine ring.

While Y may substitute at any position on the benzene ring, it preferably substitutes at the 4-position.

Particularly, a pyridazinone compound wherein, in the formula (I), $R^1$ and $R^2$ are hydrogen atoms, $R^3$ is hydrogen atom or alkyl having 1 to 4 carbon atoms, X is halogen atom, Y is halogen atom or hydrogen atom and A is alkylene having 1 to 5 carbon atoms, which is optionally substituted with hydroxyl, and its pharmacologically acceptable salt are preferable.

The pharmacologically acceptable salt of pyridazinone compound (I) includes, for example, salts with inorganic acid (e.g., hydrochloride, hydrobromide, phosphate, sulfate and the like), salts with organic acid (e.g., acetate, succinate, maleate, fumarate, malate, tartrate and the like), and the like.

The pyridazinone compound (I) can be converted to the above-mentioned salts by a conventional method.

Examples of more preferable pyridazinone compound (I) include 4-bromo-6-(3-phenylpropoxy)-5-(3-pyridylmethylamino) -3(2H)-pyridazinone, 4-chloro-6-(3-phenylpropoxy)-5-(3-pyridylmethylamino)-3(2H)-pyridazinone, 4-chloro-6-[3-(4-chlorophenyl)propoxy]-5-(3-pyridylmethylamino)-3(2H)-pyridazinone, 4-bromo-6-[3-(4-chlorophenyl)propoxy]-5-(3-pyridylmethylamino)-3(2H)-pyridazinone, 4-bromo-6-(2,2-dimethyl-3-phenylpropoxy)-5-(3-pyridylmethylamino)-3(2H)-pyridazinone, 4-chloro-6-(2,2-dimethyl-3-phenylpropoxy)-5-(3-pyridylmethylamino)-3(2H)-pyridazinone, 4-bromo-6-[3-(4-chlorophenyl)-2,2-dimethylpropoxy]-5-(3-pyridylmethylamino)-3(2H)-pyridazinone, 4-chloro-6-[3-(4-chlorophenyl)-2,2-dimethylpropoxy]-5-(3-pyridylmethylamino)-3(2H)-pyridazinone, 4-bromo-6-[3-(4-chlorophenyl)-3-hydroxypropoxy]-5 -(3-pyridylmethylamino)-3(2H)-pyridazinone, 4-chloro-6-[3-(4-chlorophenyl)-3-hydroxypropoxy]-5-(3-pyridylmethylamino)-3(2H) -pyridazinone, 4-bromo-6-[3-(4-chlorophenyl)-2-hydroxypropoxy]-5-(3-pyridylmethylamino)-3(2H)-pyridazinone and 4-chloro-6-[3-(4-chlorophenyl)-2-hydroxypropoxy]-5-(3-pyridylmethylamino)-3(2H)-pyridazinone and their pharmacologically acceptable salts.

The pyridazinone compound (I) and its pharmacologically acceptable salt in the present invention encompass stereoisomers and optical isomers.

The pyridazinone compound (I) and its pharmacologically acceptable salt are known compounds and known to be low toxic. This compound can be produced by the method described in, for example, JP-B-7-107055, U.S. Pat. No. 5,314,883, EP-A-482208, JP-A-7-252237, U.S. Pat. No. 5,750,523 and EP-A-742211, and the like.

The pyridazinone compound (I) and its pharmacologically acceptable salt in the present invention show a superior therapeutic effect on spinal canal stenosis in mammals such as human, dog, cow, horse, rabbit, mouse, rat and the like.

The mode of administration of the pyridazinone compound (I) and its pharmacologically acceptable salt is exemplified by parenteral administration such as injection (subcutaneous, intravenous, intramuscular, intraperitoneal injections), ointment, suppository, aerosol and the like, and oral administration using tablets, capsules, granules, pills, syrup, liquid, emulsion, suspension and the like.

The pyridazinone compound (I) and its pharmacologically acceptable salt can be formulated into preparations for administration by a typical method employed for producing drugs.

The tablets, capsules, granules, pills and the like for oral administration can be prepared using excipients (e.g., sucrose, lactose, glucose, starch, mannitol and the like), binders (e.g., syrup, gum arabic, gelatin, sorbitol, tragacanth, methylcellulose, polyvinylpyrrolidone and the like), disintegrants (e.g., starch, carboxymethylcellulose and its calcium salt, microcrystalline cellulose, polyethylene glycol and the like), glidants (e.g., talc, magnesium stearate, calcium stearate, silica and the like), lubricants (e.g., sodium laurate, glycerol and the like), and the like.

The injection, aerosol, syrup, liquid, emulsion, suspension and the like are produced by a conventional method using a liquid of pyridazinone compound (I) or its pharmacologically acceptable salt in, for example, water, ethyl alcohol, isopropyl alcohol, propylene glycol, 1,3-butylene glycol, polyethylene glycol and the like), a surfactant (e.g., sorbitan fatty acid ester, polyoxyethylenesorbitan fatty acid ester, polyoxyethylene fatty acid ester, polyoxyethylene ether of hydrogenated castor oil, lecithin and the like), a suspending agent (e.g., cellulose derivative such as carboxymethylcellulose sodium salt, methylcellulose and the like, natural rubbers such as tragacanth, gum arabic and the like, and the like), a preservative (e.g., p-hydroxybenzoic acid ester, benzalkonium chloride, sorbic acid salt and the like), and the like. Suppository is produced by a conventional method using, for example, polyethylene glycol, lanolin, coconut oil and the like.

The dose of the pyridazinone compound (I) and its pharmacologically acceptable salt is appropriately determined according to the age, body weight and disease state of patients. It is generally 0.001 mg–5 g/day, preferably 0.005–1000 mg/day, for a human adult, which is administered in one to several doses a day.

The present invention is explained in detail in the following by referring to Experimental Examples and Examples. The present invention is not limited by these examples in any way.

As a reagent, compound A (4-bromo-6-[3-(4-chlorophenyl)propoxy]-5-(3-pyridylmethylamino)-3(2H)- pyridazinone hydrochloride) produced by a conventional method was used.

EXPERIMENTAL EXAMPLE 1

Effects of compound A on cauda equina nerve conduction velocity, cauda equina nerve tissue blood flow and variation in cauda equina nerve tissue oxygen tension in a rabbit acute spinal canal stenosis model (1) Preparation of the Rabbit Cauda Equina Nerve Graded Constriction Model as Rabbit Acute Spinal Canal Stenosis Model Male Japanese white rabbits were fixed at the abdominal position under anesthesia by an intravenous injection of pentobarbital sodium (25 mg/kg, DAINIPPON PHARMACEUTICAL CO., LTD.) and the vertebral arch of the fifth lumbar vertebra was removed under a microscope (OLYMPUS OME) observation to expose cauda equina nerve. After the cauda equina nerve fascicle was gently ligated at one site together with a 26 G injection needle using a catgut suture (chromic catgut (thread 4-0, needle 12.9 mm), Johnson and Johnson), the injection needle was pulled out, and the dissected portion was sutured. In the sham operation group, the cauda equina nerve was only exposed and the dissected portion was sutured.

(2) Grouping and Drug Administration

The rabbits were grouped in turn into a sham operation group (6 rabbits), a solvent group (6 rabbits), a compound A (3 mg/kg) administration group (6 rabbits), a compound A (10 mg/kg) administration group (6 rabbits), a compound A (30 mg/kg) administration group (6 rabbits), and a cilostazol (300 mg/kg, the same anti-platelet drug as compound A as a control drug, Otsuka Pharmaceutical Co., Ltd.) administration group (6 rabbits).

The drug was prepared into the volume of 5 mL/kg by suspending in 0.5% methylcellulose solution, and orally administered repeatedly once a day for 7 consecutive days from the next day of the model preparation. The 0.5% methylcellulose solution (5 mL/kg) was administered in the same manner to the solvent group. Nothing was administered to the sham operation group.

(3) Evaluation Method

The next day of the final administration (8 days after model animals preparation), the model animals were anesthetized by an intravenous injection of pentobarbital sodium (25 mg/kg) and, after insertion of a tracheal catheter, fixed at the abdominal position. The rabbits were connected to a ventilator (45 times/min) and given pancuronium bromide (0.08 mg/kg, Sankyo Co., Ltd.) by an intravenous administration. The cauda equina nerve tissue blood flow in the downstream portion of the ligation site was measured transdurally using a laser blood flowmeter [ADVANCED LASER FLOWMETER, ALF2100, Advance] under the microscope observation. The cauda equina nerve tissue oxygen tension was measured at the same site using a $pO_2$ monitor (model POG-201, Unique Medical Co. Ltd.). The cauda equina nerve conduction velocity was obtained by deriving the action potential induced by a spinal electric stimulus in the upper point and lower point of the ligation site and dividing the distance between the both points by the difference in the rise latent time (SIGNAL PROCESSOR, San-ei).

(4) Statistical Processing

The obtained results are shown in mean±standard error. Using SAS (Statistical Analysis System), the following statistical analysis was performed. The sham operation group and the solvent group were compared by the Student's t-test. The effect of the drug was verified by the Dunnett's method to the solvent group as a control. In both tests, $p<0.05$ was taken as statistically significant.

(5) Results

Figure 2:
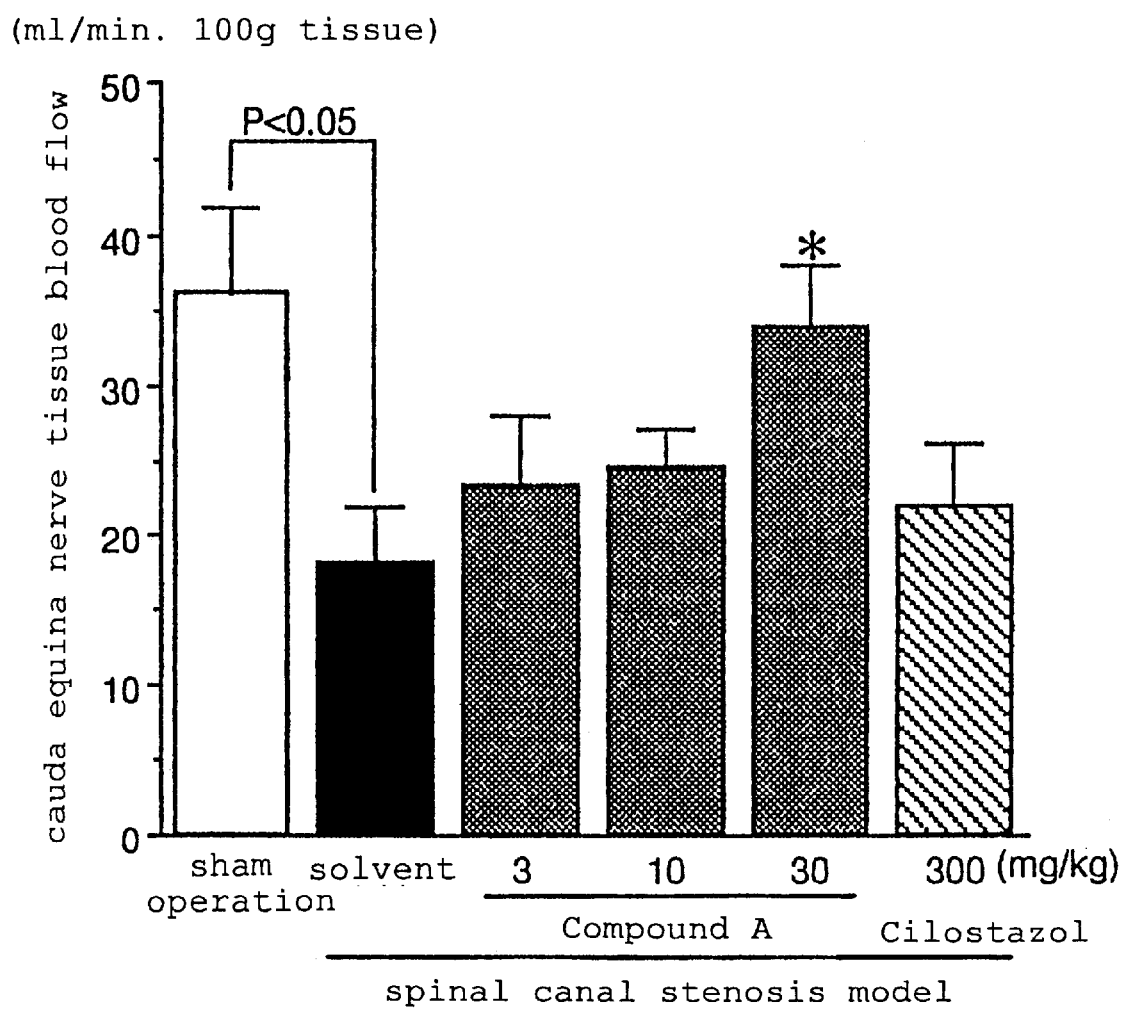
FIG. 2 shows a comparison of the effects of compound A and cilostazol on cauda equina nerve tissue blood flow in a rabbit acute spinal canal stenosis model, wherein * means that a significant difference of $p<0.05$ was obtained as a result of the Dunnett's method to a solvent group as a control. Note that $P<0.05$ means that a significant difference of $p<0.05$ was obtained as a result of the Student's t-test to a sham operation group.
Figure 3:
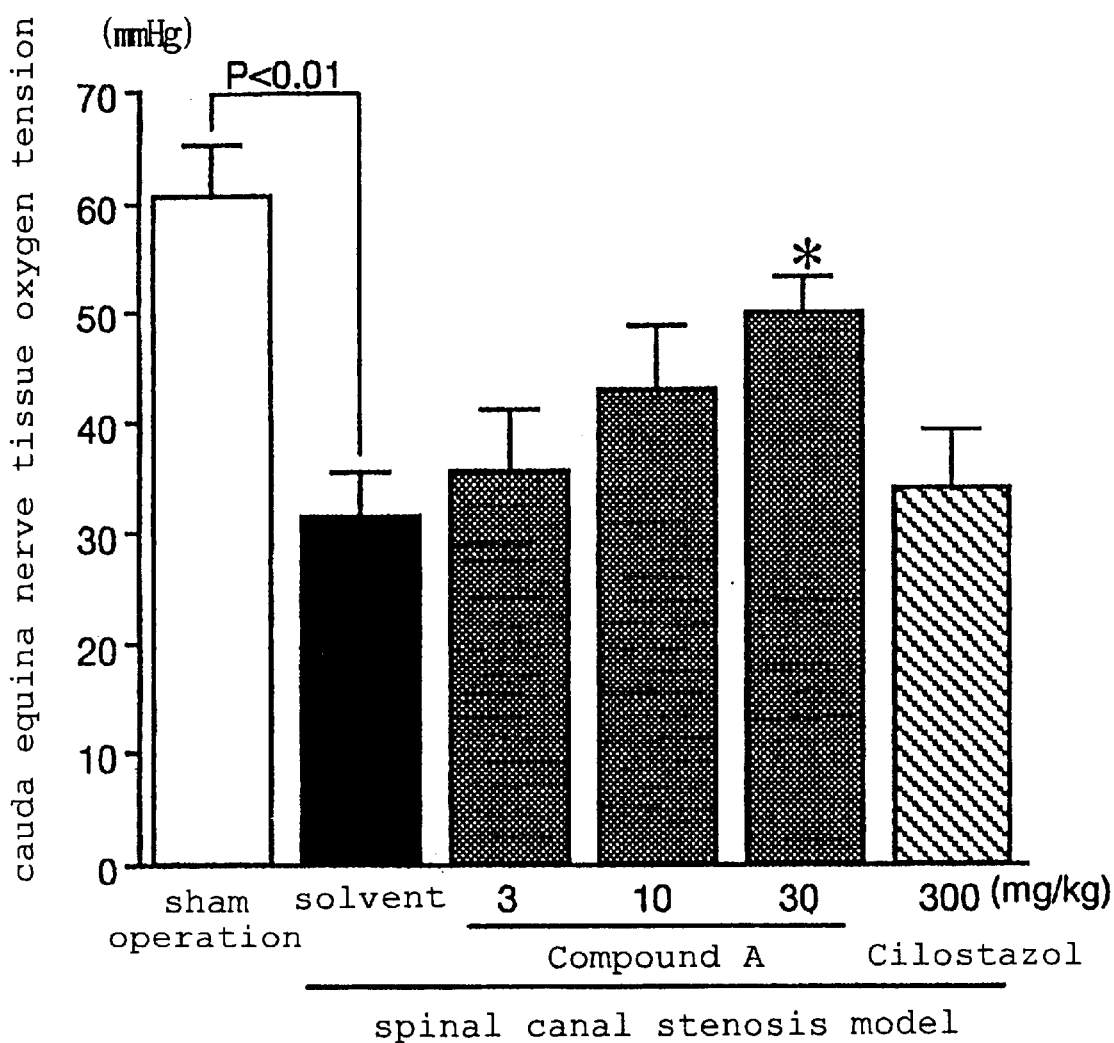
FIG. 3 shows a comparison of the effects of compound A and cilostazol on cauda equina nerve tissue oxygen tension in a rabbit acute spinal canal stenosis model, wherein * means that a significant difference of $p<0.05$ was obtained as a result of the Dunnett's method to a solvent group as a control. Note that $P<0.01$ means that a significant difference of $p<0.01$ was obtained as a result of the Student's t-test to a sham operation group.

The results are shown in Table 1, FIG. 1, FIG. 2 and FIG. 3.

TABLE 1

| Group | | Cauda equina nerve conduction velocity (cm/msec) | Cauda equina nerve tissue blood flow (ml/min. 100 g tissue) | Cauda equina nerve tissue oxygen tension (mmHg) |
| --- | --- | --- | --- | --- |
| Sham operation | | 29.237 ± 4.529 | 36.12 ± 5.65 | 60.5 ± 4.8 |
| Solvent | | 9.710 ± 1.986## | 17.98 ± 3.81# | 31.5 ± 3.9## |
| Compound A | 3 mg/kg | 20.327 ± 4.871 | 23.33 ± 4.59 | 35.5 ± 5.6 |
| | 10 mg/kg | 22.838 ± 3.571* | 24.42 ± 2.70 | 42.8 ± 5.8 |
| | 30 mg/kg | 27.098 ± 3.627** | 33.67 ± 4.21* | 49.8 ± 3.4* |
| Cilostazol 300 mg/kg | | 14.585 ± 2.606 | 21.88 ± 4.25 | 33.7 ± 5.3 |

\# $p < 0.05$, \#\# $p < 0.01$ vs. sham operation group
*$p < 0.05$, **$p < 0.01$ vs. solvent group i) Cauda Equina Nerve Conduction Velocity (Table 1, FIG. 1)

The cauda equina nerve conduction velocity was significantly decreased (delayed) in the solvent group as compared to the sham operation group. The compound A significantly lessened the decrease in a dose-dependent manner. In addition, compound A increased the conduction velocity significantly in the compound A 10 mg/kg administration group that failed to show a significant increase in the cauda equina nerve tissue blood flow. In contrast, the cilostazol (300 mg/kg) administration group did not improve the velocity.

ii) Cauda Equina Nerve Tissue Blood Flow (Table 1, FIG. 2).

The cauda equina nerve tissue blood flow was significantly decreased in the solvent group as compared to the sham operation group. The flow was significantly increased in the compound A (30 mg/kg) administration group, but not improved in the cilostazol (300 mg/kg) administration group.

iii) Cauda Equina Nerve Tissue Oxygen Tension (Table 1, FIG. 3)

The cauda equina nerve tissue oxygen tension was significantly decreased in the solvent group as compared to the sham operation group. The cilostazol (300 mg/kg) administration group did not show an increasing effect, but compound A showed a dose-dependent increase and the increase was significant in the 30 mg/kg administration group.

The above experiment results made clear as follows.

The compound A significantly suppressed the delay in the cauda equina nerve conduction velocity at 10 and 30 mg/kg administration, and significantly suppressed the decrease in the cauda equina nerve tissue blood flow and in cauda equina nerve tissue oxygen tension at 30 mg/kg administration. In contrast, cilostazol did not show a clear effect even at 300 mg/kg administration.

Therefore, it has been clarified that compound A improves the nerve conduction disorder observed in the rabbit acute spinal canal stenosis model, by partially improving the blood flow disorder of the nerve tissue and partially increasing the oxygen tension.

Inasmuch as compound A improved the cauda equina nerve conduction velocity at the dose (10 mg/kg) that did not cause a significant increase in the cauda equina nerve tissue blood flow, the possibility was suggested that other actions might have contributed to this improving effect, besides the improvement of the oxygen tension based on the increased blood flow.

EXAMPLE 1

(Tablet)

The following ingredients were mixed by a conventional method and prepared into sugar-coated tablets containing 50 mg of compound A per tablet.

| | |
|---|---|
| Compound A | 10 g |
| Lactose | 20 g |
| Starch | 5 g |
| Magnesium stearate | 0.1 g |
| Calcium carboxymethylcellulose | 7 g |
| total | 42.1 g |

EXAMPLE 2

(Capsule)

The following ingredients were mixed by a conventional method and packed in gelatin capsules to give capsules containing 50 mg of compound A per capsule.

| | |
|---|---|
| Compound A | 10 g |
| Lactose | 20 g |
| Microcrystalline cellulose | 10 g |
| Magnesium stearate | 1 g |
| total | 41 g |

EXAMPLE 3

(Ointment)

The following ingredients were mixed by a conventional method to give 1 wt % ointment.

| | |
|---|---|
| Compound A | 1 g |
| Olive oil | 20 g |
| White petrolatum | 79 g |
| total | 100 g |

EXAMPLE 4

(Aerosol Suspension)

The following ingredients (A) were mixed and the obtained mixture was charged in a container equipped with a valve. A propellant (B) was press injected at 20° C. to about 2.46–2.81 mg/cm² gauge pressure from a valve nozzle to give an aerosol suspension.

| | | |
|---|---|---|
| (A) | compound A | 0.25 wt % |
| | Isopropyl myristate | 0.10 wt % |
| | Ethanol | 26.40 wt % |
| (B) | 1,2-dichlorotetrafluoroethane and 1-chloropentafluoroethane 60–40 wt % | 73.25 wt % |

INDUSTRIAL APPLICABILITY

The pyridazinone compound (I) and its pharmacologically acceptable salt in the present invention are useful as a therapeutic agent for spinal canal stenosis.

This application is based on a patent application No. 246886/1998 filed in Japan, the contents of which are hereby incorporated by reference.

What is claimed is:

1. A method for treating spinal canal stenosis, which comprises administering an effective amount of a pyridazinone compound of the formula (I)

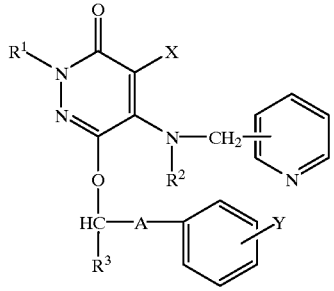

(I)

wherein $R^1$, $R^2$ and $R^3$ are each independently a hydrogen atom or a lower alkyl, X is a halogen atom, a cyano or a hydrogen atom, Y is a halogen atom, a trifluoromethyl or a hydrogen atom, and A is a $C_1$–$C_8$ alkylene optionally substituted with a hydroxyl, or its pharmacologically acceptable salt, to a mammal in need thereof.

2. The method according to claim 1, wherein $R^1$ and $R^2$ are each a hydrogen atom, $R^3$ is a hydrogen atom or a $C_1$–$C_4$ alkyl, X is a halogen atom, Y is a halogen atom or a hydrogen atom, and A is a $C_1$–$C_5$ alkylene optionally substituted with a hydroxyl, or its pharmacologically acceptable salt.

3. The method according to claim 1, wherein the pyridazinone compound of the formula (I) is 4-bromo-6-[3-(4-chlorophenyl)propoxy]-5-(3-pyridylmethylamino)-3(2H)-pyridazinone.

* * * * *